(12) United States Patent
Stirton

(10) Patent No.: US 6,623,994 B1
(45) Date of Patent: Sep. 23, 2003

(54) METHOD FOR CALIBRATING OPTICAL-BASED METROLOGY TOOLS

(75) Inventor: James Broc Stirton, Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 0 days.

(21) Appl. No.: 10/255,509

(22) Filed: Sep. 26, 2002

(51) Int. Cl.[7] ............................................... H01L 21/66
(52) U.S. Cl. ............................................ 438/14; 438/15
(58) Field of Search .......................... 438/14–16, 5–13, 438/17–18; 716/4; 118/679

(56) References Cited

U.S. PATENT DOCUMENTS

| | | | | |
|---|---|---|---|---|
| 5,393,624 A | * | 2/1995 | Ushijima | 430/30 |
| 5,555,474 A | * | 9/1996 | Ledger | 356/632 |
| 5,867,276 A | * | 2/1999 | McNeil et al. | 356/445 |
| 5,877,276 A | | 3/1999 | Borden | 356/376 |
| 5,880,838 A | * | 3/1999 | Marx et al. | 356/498 |
| 6,051,348 A | | 4/2000 | Marinaro et al. | 430/30 |
| 6,081,334 A | | 6/2000 | Grimbergen et al. | 356/357 |
| 6,100,985 A | * | 8/2000 | Scheiner et al. | 356/630 |
| 6,122,064 A | * | 9/2000 | Banet et al. | 356/630 |
| 6,245,584 B1 | * | 6/2001 | Marinaro et al. | 438/14 |
| 6,509,201 B1 | * | 1/2003 | Wright | 438/16 |

* cited by examiner

*Primary Examiner*—John F. Niebling
*Assistant Examiner*—Olivia Luk
(74) *Attorney, Agent, or Firm*—Williams, Morgan & Amerson, P.C.

(57) ABSTRACT

The present invention is generally directed to various methods for calibrating optical-based metrology tools. In one illustrative embodiment, the method comprises performing a metrology process on a specimen using an optical-based metrology tool to obtain optical characteristic data and comparing the obtained optical characteristic data to target optical characteristic data established for the specimen.

26 Claims, 2 Drawing Sheets

```
Performing a metrology process on
a specimen using an optical based      — 40
metrology tool to obtain optical
characteristic data; and
```

```
comparing the obtained optical         — 42
characteristic data to target optical
characteristic data established for
the specimen.
```

METHOD FOR CALIBRATING OPTICAL-BASED METROLOGY TOOLS

BACKGROUND OF THE INVENTION

1. Field of the Invention

This invention relates generally to semiconductor fabrication technology, and, more particularly, to a method for calibrating optical-based metrology tools.

2. Description of the Related Art

There is a constant drive within the semiconductor industry to increase the operating speed of integrated circuit devices, e.g., microprocessors, memory devices, and the like. This drive is fueled by consumer demands for computers and electronic devices that operate at increasingly greater speeds. This demand for increased speed has resulted in a continual reduction in the size of semiconductor devices, e.g., transistors. That is, many components of a typical field effect transistor (FET), e.g., channel length, junction depths, gate insulation thickness, and the like, are reduced. For example, all other things being equal, the smaller the channel length of the transistor, the faster the transistor will operate. Thus, there is a constant drive to reduce the size, or scale, of the components of a typical transistor to increase the overall speed of the transistor, as well as integrated circuit devices incorporating such transistors.

By way of background, an illustrative field effect transistor 10, as shown in FIG. 1, may be formed above a surface 11A of a semiconducting substrate or wafer 11 comprised of doped-silicon. In the process of forming integrated circuit devices, millions of transistors, such as the illustrative transistor 10 depicted in FIG. 1, are formed above a semiconducting substrate. The substrate 11 may be doped with either N-type or P-type dopant materials, for example. The transistor 10 may have a doped polycrystalline silicon (polysilicon) gate electrode 14 formed above a gate insulation layer 16. The gate electrode 14 and the gate insulation layer 16 may be separated from doped source/drain regions 22 of the transistor 10 by a dielectric sidewall spacer 20. The source/drain regions 22 for the transistor 10 may be formed by performing one or more ion implantation processes to introduce dopant atoms, e.g., arsenic or phosphorous for NMOS devices, boron for PMOS devices, into the substrate 11. Shallow trench isolation regions 18 may be provided to isolate the transistor 10 electrically from neighboring semiconductor devices, such as other transistors (not shown). Additionally, although not depicted in FIG. 1, a typical integrated circuit device is comprised of a plurality of conductive interconnections, such as conductive lines and conductive contacts or vias, positioned in multiple layers of insulating material formed above the substrate. These conductive interconnections allow electrical signals to propagate between the transistors formed above the substrate.

During the course of manufacturing integrated circuit products, a variety of optical-based metrology tools, such as ellipsometers, scatterometry-based tools, reflectometers, optical gas emission analyzers, etc., are used to obtain a variety of different types of metrology data. Such metrology data may relate to the size of various features, the thickness of one or more layers of materials, the spacing between features, etc.

As a more specific example, during the course of fabricating such integrated circuit devices, a variety of features, e.g., gate electrodes, conductive lines, openings in layers of insulating material, etc., are formed to very precisely controlled dimensions. Such dimensions are sometimes referred to as the critical dimension (CD) of the feature. It is very important in modern semiconductor processing that features be formed as accurately as possible due to the reduced size of those features in such modern devices. The gate electrode 14 has a critical dimension 12, i.e., the width of the gate electrode 14, that approximately corresponds to the channel length 13 of the device when the transistor 10 is operational. Gate electrodes 14 may now be patterned to a width 12 that is approximately 180 nm, and further reductions are planned in the future, e.g., 120 nm. Since the width 12 of the gate electrode 14 corresponds approximately to the channel length 13 of the transistor 10 when it is operational, even slight variations in the critical dimension 12 of the gate electrode 14 as fabricated may adversely affect device performance. Moreover, at a given level of a wafer, features, e.g., gate electrodes, may be formed to a variety of different critical dimensions. As another example, in manufacturing modern semiconductor devices, the thickness of various layers, e.g., gate insulation layers, is very tightly controlled such that completed devices may meet target performance specifications. For example, the thickness of the gate insulation layer 16 is very important in determining certain performance aspects of the completed transistor device. Thus, thickness measurements must, in some cases, be very accurate and very tightly controlled.

Given the importance of metrology data and tools in modern semiconductor device manufacturing, it is very important that the various metrology tools provide accurate, reliable data. Moreover, it is also important that the metrology tools be properly calibrated and maintained such that data derived through use of such metrology tools is accurate and reliable. Additionally, it is important to be able to monitor metrology processes performed in the metrology tool to determine when the process begins to degrade or drift. Such drift may be due to a variety of factors, such as the cleanliness of the tools, wear on various parts of the tool, etc.

The present invention is directed to various methods that may solve, or at least reduce, some or all of the aforementioned problems.

SUMMARY OF THE INVENTION

The present invention is generally directed to various methods for calibrating optical-based metrology tools. In one illustrative embodiment, the method comprises performing a metrology process on a specimen using an optical-based metrology tool to obtain optical characteristic data and comparing the obtained optical characteristic data to target optical characteristic data established for the specimen.

BRIEF DESCRIPTION OF THE DRAWINGS

The invention may be understood by reference to the following description taken in conjunction with the accompanying drawings, in which like reference numerals identify like elements, and in which.

Figures 1, 3:
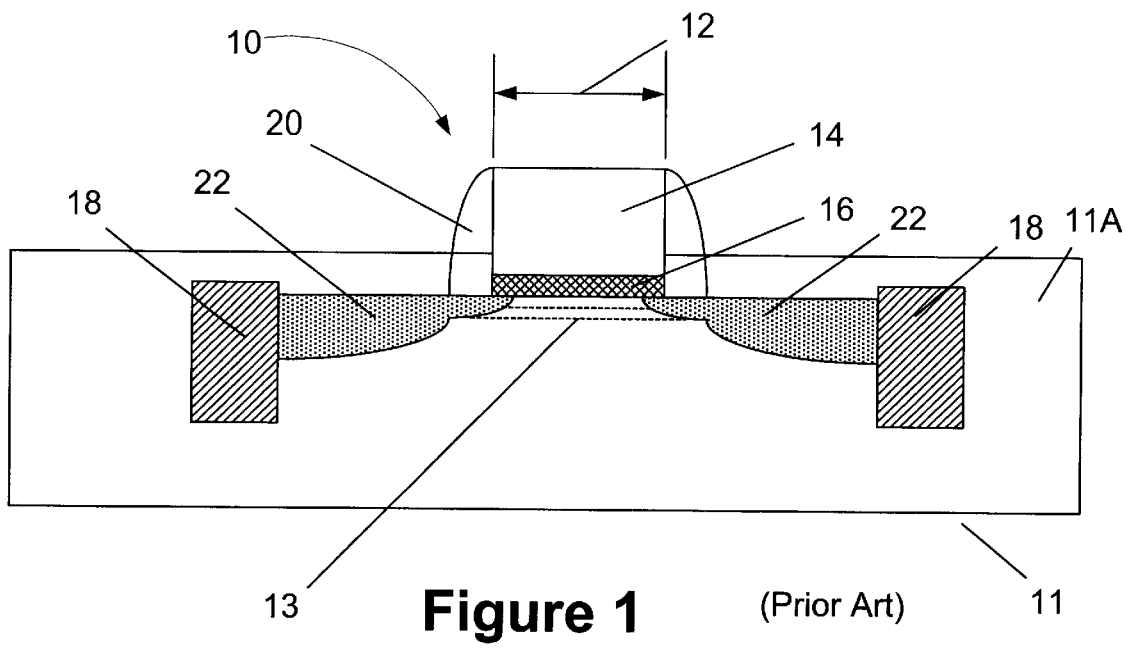
FIG. 1 is a cross-sectional view of an illustrative prior art transistor.
FIG. 3 is a depiction of one illustrative embodiment of the present invention in flowchart form.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. Although the various regions and structures of a semiconductor device are depicted in the drawings as having very precise, sharp configurations and profiles, those skilled in the art recognize that, in reality, these regions and structures are not as precise as indicated in the drawings. Additionally, the relative sizes of the various features and doped regions depicted in the drawings may be exaggerated or reduced as compared to the size of those features or regions on fabricated devices. Nevertheless, the attached drawings are included to describe and explain illustrative examples of the present invention. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

In general, the present invention is directed to various methods for calibrating optical-based metrology tools. As will be readily apparent to those skilled in the art upon a complete reading of the present application, the methods disclosed herein are applicable to obtaining a vast variety of metrology data during the course of manufacturing a variety of integrated circuit products and devices, e.g., transistors, memory cells, microprocessors, application specific circuits, etc. Moreover, the present invention may be employed in industries other than semiconductor manufacturing. Thus, the illustrative examples relating to semiconducting manufacturing described herein should not be considered a limitation of the present invention unless such limitations are expressly set forth in the appended claims.

Figure 2:
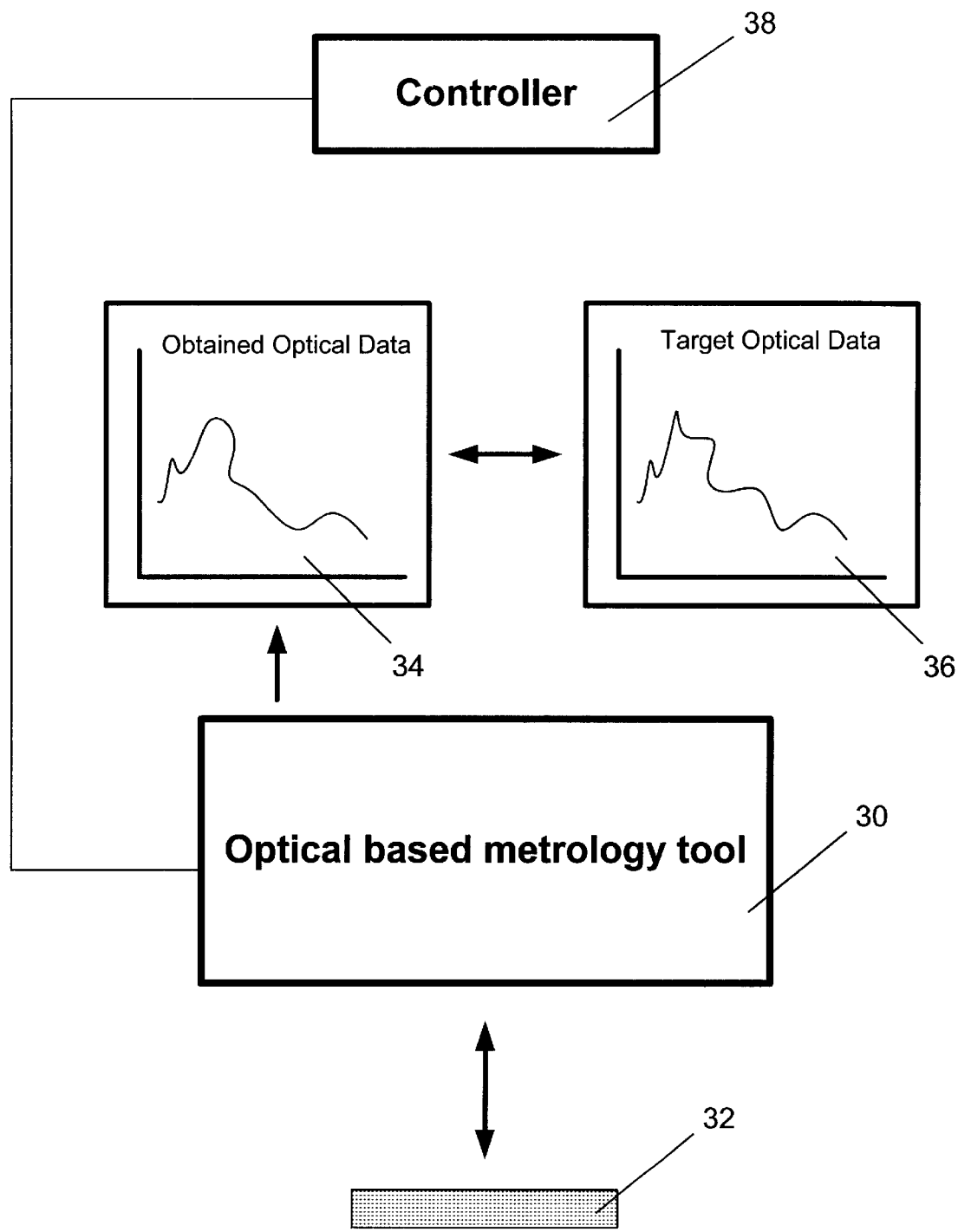
FIG. 2 is a schematic, block diagram of an illustrative optical-based metrology tool that may be employed in the context of the present invention.

FIG. 2 is a schematic, block diagram depiction of an optical-based metrology tool 30 that may be used to obtain metrology data regarding some aspect of the illustrative specimen 32. Based upon the measurement of the specimen 32, the optical-based metrology tool 30 outputs data, e.g., raw spectral data, as indicated in block 34. In general, in one embodiment, the present invention involves, among other things, comparing the obtained optical characteristic data in block 34 to target or "golden" optical characteristic data established for the specimen 32, indicated in block 36. Based upon a comparison of the obtained optical characteristic data 34 and the target optical characteristic data 36, various activities or actions may be undertaken as described more fully below.

The present invention may be used with a variety of different optical-based metrology tools 30. In general, the optical-based metrology tool 30 may be any type of metrology tool in which the tool uses at least one light source to illuminate an object, e.g., a portion of a semiconducting substrate, and collects and analyzes light reflected from or off the illuminated object. In the context of semiconductor manufacturing operations, the optical-based metrology tool 30 may be used to obtain metrology data regarding any of a variety of different aspects of semiconductor processing operations, such as line width, trench width, feature cross-sectional profiles, the thickness of one or more layers of material, the reflectance of a layer of material, the roughness of a surface, a dispersion coefficient (n+k), etc.

In some cases, the optical-based metrology tool 30 outputs raw spectral data as a result of the measurement activities. For example, the optical-based metrology tool 30 may be a reflectometer, an ellipsometer, a spectroscopic ellipsometer, an optical gas emission analyzer, etc. The optical-based metrology tool 30 may also be any of a variety of different types of scatterometry-based tools wherein a substrate is illuminated and the reflected light spectra is measured or analyzed, e.g., so-called 2θ-type systems and lens-type scatterometry tools. Such a scatterometer may use white light, or some other wavelength or combination of wavelengths, depending on the specific implementation. Typically, a scatterometry tool will generate an incident beam that has a wide spectral composition and wherein the intensity of the light changes slowly in comparison to changes in wavelength. The angle of incidence of the light may also vary, depending on the specific implementation. The optical characteristic traces generated by the scatterometry tool may be based upon a comparison of light intensity to wavelength (for white light, fixed angle type scatterometry tools) or a comparison of intensity to incident angle (for angle resolved systems that use a single light source). Additionally, a light source and a detector of the scatterometry tool may be arranged in a concentric circle configuration, with the light source illuminating an object. The intensity of the reflected light may be measured as s- and p-polarization over either multiple angles or at multiple wavelengths. A scatterometry tool will also typically include optical hardware, such as an ellipsometer or reflectometer, and a data processing unit loaded with a scatterometry software application for processing data collected by the optical hardware. For example, the optical hardware may include a Model OP5230 or OP5240 with a spectroscopic ellipsometer offered by Thermawave, Inc. of Fremont, Calif. The data processing unit may comprise a profile application server manufactured by Timbre Technologies, a fully owned subsidiary of Tokyo Electron America, Inc. of Austin, Tex. and distributed by Thermawave, Inc.

The specimen 32 is a standard or reference specimen that is measured by the optical-based metrology tool 30 to establish the target optical characteristic data 36. The specimen 32 may be tailored for any type of feature that can be measured with the optical-based metrology tool 30. For example, the specimen 32 may be a grating structure comprised of a plurality of lines having a known size and periodicity formed in a semiconducting substrate. Alternatively, the specimen 32 may have a layer of material of a known thickness formed above a semiconducting substrate or it may be a known gas specimen.

From the foregoing, it should be understood that the specimen 32 depicted in the drawing is representative in nature. The size and configuration of the specimen 32 may also vary. Lastly, any desired characteristic of the specimen 32 may be measured using the optical-based metrology tool 30. For example, where the specimen is comprised of one or more lines, the optical-based metrology tool 30 may be used to determine a cross-sectional profile of the line or a critical dimension of the line. In the case where the specimen 32 is comprised of a layer of material, a variety of characteristics of the layer of material may be examined, e.g., thickness, reflectance, surface roughness, etc. Such characteristics may also include a dispersion coefficient (n+k).

Moreover, in the illustrative embodiment depicted in FIG. 2, the obtained optical characteristic data 34 and the target optical characteristic data 36 take the form of a plot or trace of the optical data. However, as will be recognized by those skilled in the art after a complete reading of the present application, the obtained optical characteristic data 34 and the target optical characteristic data 36 may be presented in any form, e.g., a tabular form, etc.

The target optical characteristic data 36 may be established by measuring the specimen 32 at one or more locations using the optical-based metrology tool 30. For example, the specimen 32 may be a semiconducting substrate having a grating structure comprised of a plurality of gate electrode structures, wherein the gate electrode structures have a known critical dimension or profile. The target optical characteristic data 36 may be established by a variety of methods. For example, in one aspect, the optical-based metrology tool 30 may be calibrated at any time using the methods disclosed herein. That is, in some cases, the methods disclosed herein may be used to look at process drift or degradation. In that case, relative changes between separate measurements may be the only thing of interest, i.e., absolute measurement may be of little or no interest. In this situation, the specimen 32 may be initially measured to establish a target optical characteristic data 36 for the specimen 32. Subsequent measurements of the specimen 32 may be made using the optical-based metrology tool 30 and the obtained optical characteristic data 34 may be compared to the target optical characteristic data 36 to determine if a variance between the compared data exists and, in some cases, the magnitude of that variance.

As set forth previously, metrology tool data is very important to modern semiconductor manufacturing facilities. Metrology tools are frequently, and in some cases constantly, used in the manufacturing process. As a result, over time, the performance and capabilities of such a metrology tool may erode or drift. Given the device's dimensions involved in manufacturing modern integrated circuit devices, even very slight drifts in the performance of metrology tools may adversely impact the ability to manufacture integrated circuit products to the stringent performance standards required for many high performance integrated circuit products.

To that end, efforts are made to identify and limit process drift in metrology tools. In some cases, such efforts include measuring a specimen having a known feature size and comparing the measured feature size, as determined during the measurement process, with the known feature size of the specimen. If the measured values are within a given range of the values of the standard, then the operation of the optical-based metrology tool 30 is deemed to be acceptable. Typically, the raw optical metrology data obtained by the optical-based metrology tool 30 is compared to a library of optical characteristic traces, each of which corresponds to a physical dimension of a known sample. The raw optical data is compared to the library of traces and, based upon the closest match, the raw optical data is deemed to match or correspond to one of the optical traces in the library. Accordingly, the value or metric, e.g., thickness, length, etc., associated with the matched trace is also indicated as the value associated with the raw optical data obtained during the measurement process.

While the above-referenced technique may produce acceptable results in some circumstances, it has inherent drawbacks that may adversely impact the ability to control optical-based metrology processes as tightly as would be desired in present-day manufacturing environments where great precision is required. For example, the present invention involves a comparison of the raw optical characteristic data 34 obtained by the optical-based metrology tool 30 with the target optical characteristic data 36. That is, in the present invention, the performance of the optical-based metrology tool 30 is determined by comparing the sets or collections of optical characteristic data as opposed to comparing numerical outputs associated with an optical characteristic trace after it has been matched to a trace from a library. Simply put, the present methodology may eliminate or reduce errors inherent in the library matching process.

As a very specific example, a first measurement may be taken with the optical-based metrology tool 30 and the resulting raw optical characteristic data may be compared to a library of optical traces and ultimately matched to the closest optical trace in the library. The numerical value associated with the matched trace from the library is then output as the value for the optical data obtained by the optical-based metrology tool 30. The optical-based metrology tool 30 may then be used to measure another object or wafer, and the raw spectral data from the second measurement may be compared to the traces in the library. However, even if the optical-based metrology tool 30 is experiencing drift, i.e., even if the raw spectral data for the second measurement differs from the data for the first measurement, the raw spectral data for the second measurement may still be matched to the same trace in the library as was the first set of optical data. That is, although the metrology process may be drifting, the errors inherent in matching a trace from a library may mask the process drift.

In the present invention, the optical-based metrology tool 30 is calibrated by comparing optical characteristic data. Using the present invention, errors inherent in the library matching methodology disclosed above are eliminated. In short, monitoring the performance of the optical-based metrology tool 30 using raw optical data provides greater sensitivity when examining the performance of the optical-based metrology tool 30.

In operation, the present invention involves measuring a specimen 32 using the optical-based metrology tool 30, and comparing the optical metrology data 34 from this measurement to target optical characteristic data 36 established for the specimen 32. The comparison between the two sets of optical characteristic data may be performed using a variety of analytical techniques known to those skilled in the art, such as mean square error (MSE). If a variance or difference is detected between the obtained optical characteristic data 34 and the target optical characteristic data 36, then one or more actions may be taken. If the variance is less than a preselected limit, then the optical-based metrology tool 30 may be deemed to be fully operational. If the variance is greater than a preselected limit, then the tool 30 may be deemed to be unfit for further service and taken off-line. The variance may be such that the optical-based metrology tool 30 may be disqualified for use on highly sensitive metrology applications, e.g., gate electrode widths, thickness of gate insulation layers, etc., while still being eligible for use on less sensitive metrology applications, e.g., non-critical implant processes or non-critical layers. The variance between the sets of optical data may also be used to initiate or modify maintenance procedures. For example, the rate of change in the variance of multiple measurements may indicate that a pre-planned maintenance schedule should be advanced.

The optical-based metrology tool 30 may be calibrated on any desired basis. For example, the optical-based metrology tool may be calibrated on a daily, weekly or monthly basis. Alternatively, the optical-based metrology tool 30 may be calibrated on the basis of the number of wafers processed through the metrology tool 30. A variety of different schemes may be devised for calibrating the optical-based metrology tool 30.

As shown in FIG. 2, a controller 38 may be used in the collection and analysis of the optical data described herein. The controller 38 may be any type of device capable of executing instructions. The controller 38 may be a stand-alone computer or it may be resident on the optical-based metrology tool 30. Based upon receipt and analysis of the optical data described herein, the computer 38 may initiate various control actions as described herein.

Portions of the invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be understood, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the actions and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

The present invention is generally directed to various methods for calibrating optical-based metrology tools. FIG. 3 depicts one illustrative embodiment of the present invention in flowchart form. As shown therein, the method comprises performing a metrology process on a specimen using an optical-based metrology tool to obtain optical characteristic data, as set forth at block 40, and comparing the obtained optical characteristic data to target optical characteristic data established for the specimen, as indicated in block 42.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method of qualifying an optical-based metrology tool, comprising:

performing a metrology process on a specimen using said optical-based metrology tool to obtain optical characteristic data;

comparing aid obtained optical characteristic data to target optical characteristic data established for said specimen; and initiating a maintenance procedure on said optical-based metrology tool based upon a variance between said obtained optical characteristic data and said target optical characteristic data.

2. The method of claim 1, wherein said optical-based metrology tool is comprised of at least one of a reflectometer, an ellipsometer, a spectroscopic ellipsometer and a scatterometer.

3. The method of claim 1, wherein said specimen is comprised of a semiconducting substrate.

4. The method of claim 1, wherein said specimen comprises a semiconducting substrate and wherein said obtained optical characteristic data is directed to at least one of a size of a feature formed above said substrate, a width of a line, a width of a trench, a thickness of at least one layer of material, a cross-sectional profile of a feature, and a dispersion coefficient.

5. The method of claim 1, further comprising determining if a variance exists between said obtained optical characteristic data and said target optical characteristic data.

6. The method of claim 1, further comprising determining if a variance between said obtained optical characteristic data and said target optical characteristic data is less than a preselected value.

7. The method of claim 1, further comprising determining if a variance between said obtained optical characteristic data and said target optical characteristic data is greater than a preselected value.

8. The method of claim 1, further comprising determining if a variance between said obtained optical characteristic data and said target optical characteristic data is within preselected allowable limits.

9. The method of claim 1, further comprising limiting use of said optical-based metrology tool based upon a variance between said obtained optical characteristic data and said target optical characteristic data.

10. A method of qualifying an optical-based metrology tool, comprising:

performing a metrology process on a specimen using said optical-based metrology tool to obtain optical characteristic data;

comparing said obtained optical characteristic data to target optical characteristic data established for said specimen;

determining if a variance exists between said obtained optical characteristic data and said target optical characteristic data; and removing said optical-based metrology tool from service based upon the existence of a determined variance between said obtained optical characteristic data and said target optical characteristic data.

11. The method of claim 10, wherein said optical-based metrology tool is comprised of at least one of a reflectometer, an ellipsometer, a spectroscopic ellipsometer and a scatterometer.

12. The method of claim 10, wherein said specimen comprises a semiconducting substrate and wherein said obtained optical characteristic data is directed to at least one of a size of a feature formed above said substrate, a width of a line, a width of a trench, a thickness of at least one layer of material, a cross-sectional profile of a feature, and a dispersion coefficient.

13. The method of claim 10, wherein determining if said variance exists between the obtained optical characteristic data and the target optical characteristic data further comprises determining if a variance between said obtained optical characteristic data and said target optical characteristic data is less than a preselected value.

14. The method of claim 10, wherein determining if said variance exists between the obtained optical characteristic data and the target optical characteristic data further comprises determining if a variance between said obtained optical characteristic data and said target optical characteristic data is greater than a preselected value.

15. The method of claim 10, wherein determining if said variance exists between the obtained optical characteristic data and the target optical characteristic data further comprises determining if a variance between said obtained optical characteristic data and said target optical characteristic data is within preselected allowable limits.

16. A method of qualifying an optical-based metrology tool, comprising:

performing a metrology process on a specimen using said optical-based metrology tool to obtain optical characteristic data;

comparing said obtained optical characteristic data to target optical characteristic data established for said specimen; and removing said optical-based metrology tool from service if a variance between said obtained optical characteristic data and said target optical characteristic data exceeds a preselected limit.

17. The method of claim 16, wherein said optical-based metrology tool is comprised of at least one of a reflectometer, an ellipsometer, a spectroscopic ellipsometer and a scatterometer.

18. The method of claim 16, wherein said specimen is comprised of a semiconducting substrate.

19. The method of claim 16, wherein said specimen comprises a semiconducting substrate and wherein said obtained optical characteristic data is directed to at least one of a size of a feature formed above said substrate, a width of a line, a width of a trench, a thickness of at least one layer of material, a cross-sectional profile of a feature, and a dispersion coefficient.

20. The method of claim 16, wherein removing said optical-based metrology tool from service comprises limiting use of said optical-based metrology tool based upon said variance between said obtained optical characteristic data and said target optical characteristic data.

21. The method of claim 16, further comprising initiating a maintenance procedure on said optical-based metrology tool based upon said variance between said obtained optical characteristic data and said target optical characteristic data.

22. A method of qualifying an optical-based metrology tool, comprising:

performing a metrology process on a specimen using said optical-based metrology tool to obtain optical characteristic data;

comparing said obtained optical characteristic data to target optical characteristic data established for said specimen; and limiting use of said optical-based metrology tool to specific metrology applications based upon a variance between said obtained optical characteristic data and said target optical characteristic data.

23. The method of claim 22, wherein said optical-based metrology tool is comprised of at least one of a reflectometer, an ellipsometer, a spectroscopic ellipsometer and a scatterometer.

24. The method of claim 22, wherein said specimen is comprised of a semiconducting substrate.

25. The method of claim 22, wherein said specimen comprises a semiconducting substrate and wherein said obtained optical characteristic data is directed to at least one of a size of a feature formed above said substrate, a width of a line, a width of a trench, a thickness of at least one layer of material, a cross-sectional profile of a feature, and a dispersion coefficient.

26. The method of claim 22, further comprising initiating a maintenance procedure on said optical-based metrology tool based upon said variance between said obtained optical characteristic data and said target optical characteristic data.

* * * * *

UNITED STATES PATENT AND TRADEMARK OFFICE
CERTIFICATE OF CORRECTION

PATENT NO.     : 6,623,994 B1                                               Page 1 of 1
DATED          : September 23, 2003
INVENTOR(S)    : James Broc Stirton It is certified that error appears in the above-identified patent and that said Letters Patent is hereby corrected as shown below:

Column 8,
Line 30, "comparing aid" should be -- comparing said --.

Signed and Sealed this

Fourth Day of November, 2003

JAMES E. ROGAN
*Director of the United States Patent and Trademark Office*